United States Patent [19]
Asbaghi

[11] Patent Number: 5,688,241
[45] Date of Patent: Nov. 18, 1997

[54] AUTOMATIC NON-REUSABLE NEEDLE GUARD

[76] Inventor: Hooman Ali Asbaghi, 3956 Nobel Dr., #104, San Diego, Calif. 92122

[21] Appl. No.: 632,010

[22] Filed: Apr. 15, 1996

[51] Int. Cl.⁶ ............................................. A61M 5/00
[52] U.S. Cl. ............................................. 604/110; 604/198
[58] Field of Search ............................. 604/110, 187, 604/192, 198, 263

[56] References Cited

U.S. PATENT DOCUMENTS

| | | | |
|---|---|---|---|
| 4,813,940 | 3/1989 | Parry | 604/198 |
| 4,894,055 | 1/1990 | Sudnak | 604/263 X |
| 4,911,693 | 3/1990 | Paris | 604/192 |
| 5,104,384 | 4/1992 | Parry | 604/192 |
| 5,292,314 | 3/1994 | D'Alessio et al. | 604/198 |
| 5,295,975 | 3/1994 | Lockwood, Jr. et al. | 604/198 |
| 5,364,362 | 11/1994 | Schulz | 604/192 X |
| 5,389,085 | 2/1995 | D'Alessio et al. | 604/198 |

*Primary Examiner*—John D. Yasko
*Attorney, Agent, or Firm*—Charles F. Reidelbach, Jr.

[57] ABSTRACT

The automatic non-reusable needle guard includes an outer cylinder adaptable to a needle or needle retaining device such as a syringe. An inner cylinder is operable with the outer cylinder for movement of the inner cylinder from an initial retractable position to a released or armed position and further to an extended irreversible position. The mechanism which provides movement of the inner cylinder relative to the outer cylinder incorporates a track formed in the inner surface of the outer cylinder. The inner cylinder incorporates at least one protruding member which may be formed on the outer surface of the inner cylinder and is positioned in the track for guiding the inner cylinder from the initial usable position to the released position and further to the extended irreversible position. A spring is disposed within the inner cylinder and coupled to the outer cylinder for urging the inner cylinder away from the outer cylinder thereby moving the inner cylinder from the released or armed position to the extended irreversible position. The needle guard also includes a locking mechanism for preventing removal or retraction of the inner cylinder after the inner cylinder is fully extended in the extended irreversible position. The outer cylinder has a lip portion for preventing removal of the inner cylinder from the outer cylinder. At least one flexible flap positioned on the outer surface of the inner cylinder prevents retraction of the inner cylinder after use.

21 Claims, 2 Drawing Sheets

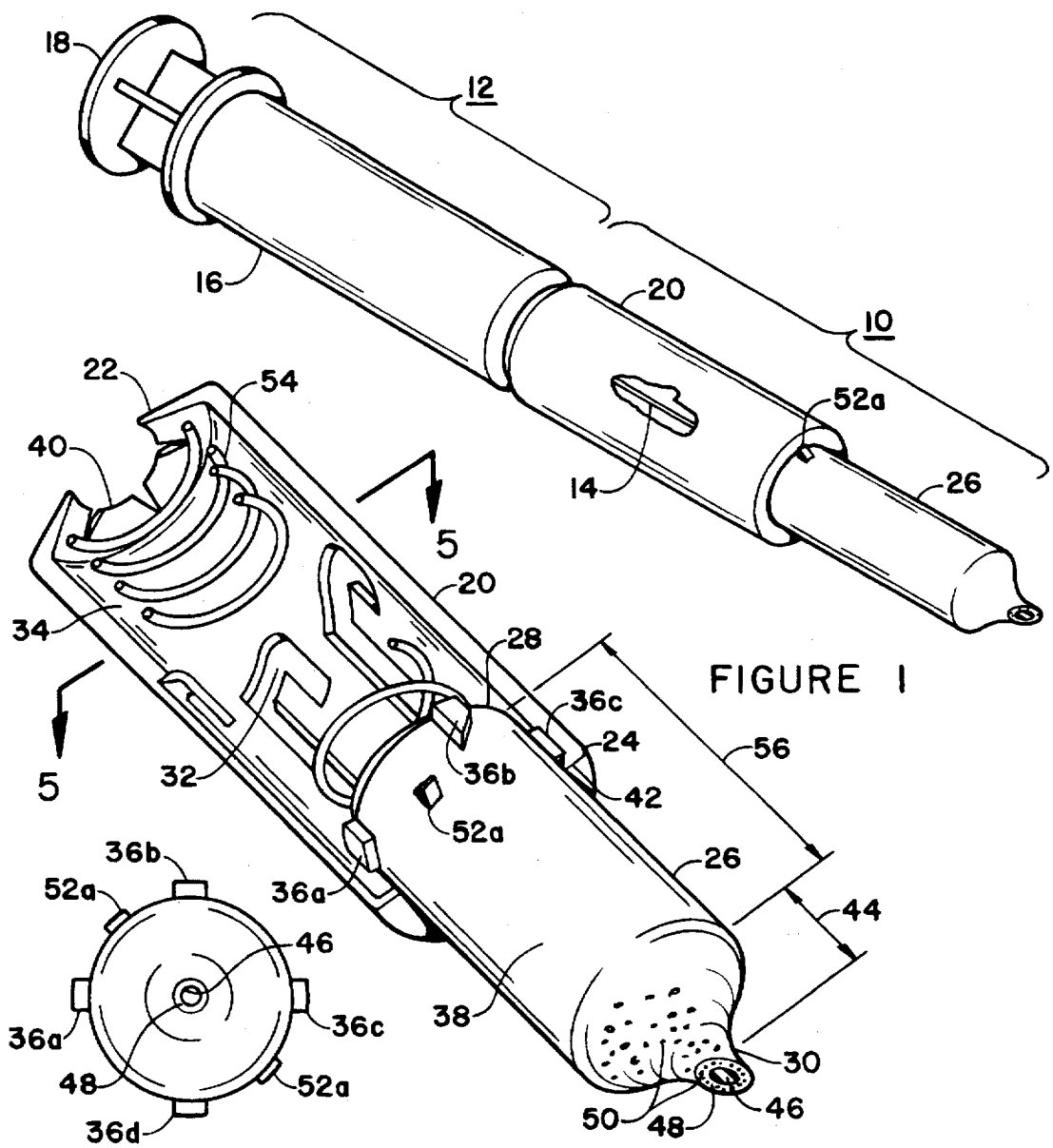
FIGURE 1
FIGURE 4
FIGURE 2
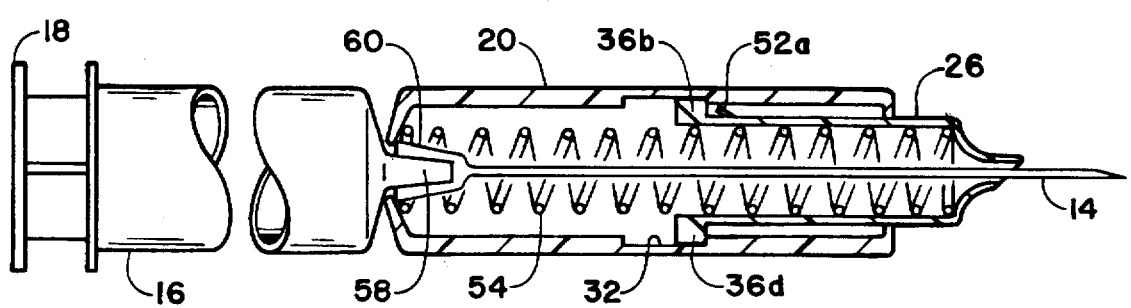
FIGURE 3

AUTOMATIC NON-REUSABLE NEEDLE GUARD

FIELD OF THE INVENTION

The present invention pertains to a safety needle guard apparatus and method for preventing the spread and transmission of infectious bloodborne diseases. More specifically, the present invention provides an automatically extending safety needle guard which systematically implements a permanent locking function to prevent re-use of contaminated needles. The present invention eliminates the human element in the needle protection process by providing a fully automatic single use system.

BACKGROUND OF THE INVENTION

As is widely known, many infectious diseases including HIV, hepatitis B virus, malaria and tuberculosis are spread through invasive contact with bodily fluids from infected individuals. One well known method of transmission of the above diseases is by accidental needlesticks from needles that have come in contact with blood and other bodily fluids from infected individuals.

The Center for Disease Control and Prevention has recently reported that 86% of reported occupational HIV exposures are caused by needlesticks from hollow-bore needles. Medical professionals are understandably apprehensive about working with needles, although this simply cannot be avoided in their particular line of work.

In light of the above, hospitals, and other users of needles, have established systems and rules for the control of the use of and disposition of needles. Institutions spend millions of dollars on training and retraining healthcare workers in safe work practices to avoid or minimize their exposure to contaminated needles. Despite these efforts, about one million needlesticks still occur every year, resulting in the deaths of hundreds of heathcare workers.

Another well known method of transmission of the above diseases is the re-use of needles by drug abusers and the like who commonly share infected needles despite the severe consequences. Accordingly, needle protection devices and methods are becoming ever more common to prevent the spread of disease by the use and re-use of infected needles.

Currently, several methods are used for minimizing the above mentioned problems associated with the use and re-use of needles. For example, hospitals often provide a method for manually clipping off the used needle from the syringe and containing the needle portion in certain designated containers. Another method commonly used is manually extending a safety shield or cover over the needle, before and after it is used. Although these systems may provide a partial solution, they rely on a human being to put on, take off, and put back on the safety shield back on before discarding the needle. Often, humans are careless and a used needle remains exposed. Such exposed needles create the risk of the spread of infectious diseases.

The avoidance of human involvement in the needle protection process has been addressed and attempted by some. For example, a recently issued patent purported to include an "automatic" needle protector (see U.S. Pat. No. 5,389,085, entitled Automatic Needle Protector, issuing to International Medical Consultants, Inc.). However, this device does not solve the above mentioned problems because it still requires and teaches human involvement in the needle protection process and does not prevent further re-use of the needle and initial use. For example, in column 2, lines 45–51, the above mentioned patent discloses, "[t]he needle protector is armed by [manually] rotating the cover to move the lug from the entrance position along the angled portion and to the armed position." Furthermore, in column 9, lines 15–20, the above mentioned patent states "once the lug has returned to the entrance position, the device may be reactivated by re-arming the device for further use." Accordingly, this device can be reused as many times as desired.

There is a serious need for an automatic needle guard which further minimizes human intervention by eliminating manual preparation of the needle guard prior to needle administration and which prevent further use.

SUMMARY OF THE INVENTION

It is an object of the present invention to provide an automatic needle guard which minimizes human involvement by eliminating manual preparation of the needle guard prior to needle administration and which prevents further use of the needle after the initial use.

The present invention provides an automatic non-reusable safety needle guard for use before, during and after needle administration. The needle guard includes a first or outer cylinder adaptable, either attached or integral, to a needle or needle retaining device such as a syringe. The outer cylinder has a proximal and distal end, wherein the proximal end is coupled to the needle and the distal end has an aperture for slidable movement of a second or inner cylinder therethrough.

The second or inner cylinder is contained within and operable with the first cylinder for movement of the second cylinder from an initial usable or retractable position to a released or armed position and further to an extended irreversible position. The inner cylinder also has an aperture extending longitudinally from a proximal end to a distal end for passage of a needle therethrough.

A portion of the inner cylinder proximate to the distal end decreases in diameter to substantially conform to the diameter of the needle. The distal end of the inner cylinder may have an angled or beveled tip with an adhesive or abrasive type material distributed thereon to encourage retraction of the inner cylinder during needle administration. The adhesive or abrasive material bonds the tip of the inner cylinder to the skin of a receiving body to prevent slippage.

Prior to insertion or administration of a needle into a receiving body, the inner cylinder is maintained in an initial usable or retractable position. During insertion of the needle into a receiving body, a built-in mechanism automatically releases or arms the inner cylinder from the initial usable or retractable position. Subsequently, the mechanism forces the inner cylinder to the extended irreversible position as the needle is withdrawn from the body.

The mechanism which provides movement of the inner cylinder relative to the outer cylinder as described incorporates several working components. A track formed in the inner surface of the outer cylinder. The inner cylinder incorporates at least one protruding member or lug which may be formed on the outer surface of the inner cylinder. The protruding members or lugs may be positioned proximate to the proximal end of the inner cylinder to provide increased needle coverage prior to needle administration. The lug is positioned in the track for guiding the inner cylinder from the initial usable position to the released or armed position, and then to the extended irreversible position. A spring is disposed within the inner cylinder and coupled to the proximal end of the outer cylinder for urging the inner cylinder from the outer cylinder. As a result, the inner cylinder moves from the armed or released position to the extended irreversible position.

The needle guard also includes a locking mechanism for preventing removal or retraction of the inner cylinder after the inner cylinder is fully extended in the extended irreversible position. The distal end of the outer cylinder has a lip portion for preventing removal of the inner cylinder from said outer cylinder. At least one flexible flap positioned on the outer surface of the inner cylinder prevent retraction of the inner cylinder.

The present invention also teaches a method for providing an automatic non-reusable needle. The steps of the method include adapting a proximal end of an outer cylinder to a needle retaining device and positioning the inner cylinder in the outer cylinder for movement of the inner cylinder through a distal end of the outer cylinder. The steps further include providing a spring between a proximal end of the inner cylinder and the outer cylinder for urging the inner cylinder away from the proximal end of the outer cylinder. Additional steps include maintaining the inner cylinder in an initial usable position prior to administration of the needle, arming the inner cylinder during insertion of the needle into a body, and finally extending the inner cylinder to an extended irreversible position during withdraw of the needle from the body. The method concludes by automatically locking the inner cylinder in the extended irreversible position after the needle is fully withdrawn.

BRIEF DESCRIPTION OF THE DRAWINGS

FIG. 1 is a perspective view of the present invention assembled with a needle retaining device and in a extended irreversible position;

FIG. 2 is an isometric view of the present invention with the outer cylinder cut away to illustrate the mechanism operation;

FIG. 3 is a longitudinal cross sectional view of the present invention assembled with a needle retaining device and in an initial usable or retracted position;

FIG. 4 is an end view of the inner cylinder;

DESCRIPTION OF THE PREFERRED EMBODIMENT

Figure 5:
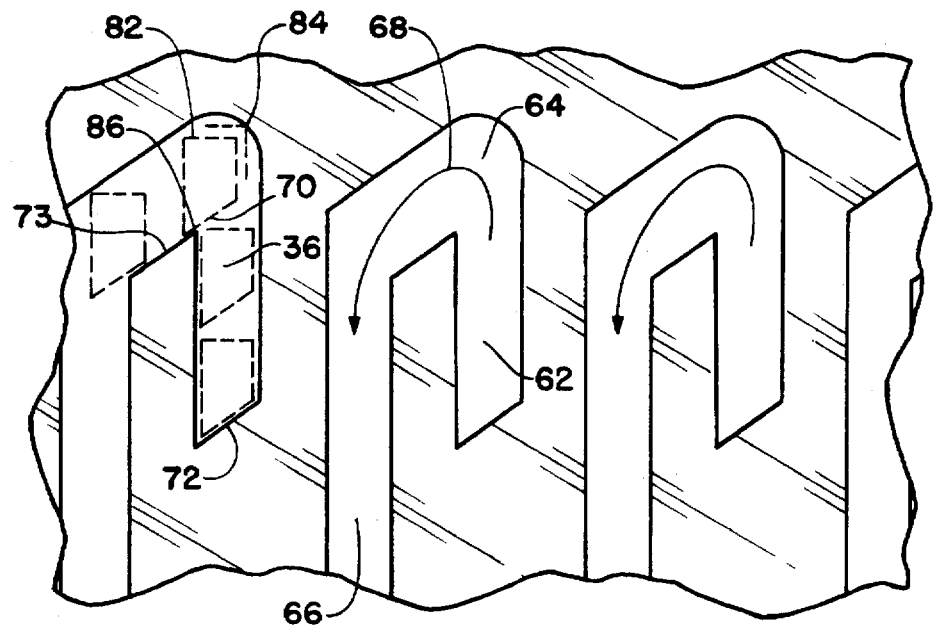
FIG. 5 is an exploded view of the outer cylinder track assembly taken at lines 5—5 of FIG. 2.

The present invention is an automatic non-reusable needle guard 10. The needle guard 10 has many applications and environments, one of which is shown in FIG. 1. In the preferred embodiment, a needle guard 10 is assembled to a needle retaining device 12. Although the needle retaining device 12 shown in FIG. 1 is a syringe 16 and associated syringe plunger 18, the needle retaining device 12 may be any well known or standard device for retaining a needle 14. The length of the retaining device used will vary with the length and size of the needle, which varies according to its use.

Referring now to FIG. 2, the needle guard 10 has multiple working components which structurally cooperate with one another to produce an automatic non-reusable needle guard function. One component of the needle guard 10 is an outer cylinder 20 having a proximal end 22 and a distal end 24. The outer cylinder 20, as well as most of the rest of the needle guard 10, may be made of any well known material such as plastic or metal. Additionally, for ease of visibility of the needle 14 and/or track 32, it may be useful to manufacture components of the device using a clear or translucent plastic or plastic like material.

In the preferred embodiment, the proximal end 22 of outer cylinder 20 is attachable to the needle retaining device 12 by way of rigid tabs 40. It should be noted however, that outer cylinder 20 can be adaptable to any standard needle 14 or needle retaining device 12 by any other means well known in the art. In fact, outer cylinder 20 may be integrally formed directly to needle 14 or needle retaining device 12. The length of the needle 14 will be dependant on the length of the needle guard 10 in relation to the amount of needle 14 required for the particular use. If a standard needle retaining device 12 is used, the needle 14 of the device will have to be extended to overcome the amount of needle covered by needle guard 10.

Positioned within the outer cylinder 20 is an inner cylinder 26 having a proximal end 28 and a distal end 30. Multiple tracks 32 are formed in the inner surface 34 of outer cylinder 20 for guiding the movement of inner cylinder 26 through the distal end 24 of outer cylinder 20. Multiple lugs 36a-d, formed on the outer surface 38 of inner cylinder 26, are positioned in respective tracks 32 of outer cylinder 20. FIG. 4 shows the preferred positioning of lugs 36a-d relative to the perimeter of inner cylinder 26. Although the preferred embodiment illustrates the use of four lugs, more or less may be used as desired for ease of manufacture.

The distal end 24 of outer cylinder 20 has a lip portion 42 for maintaining the inner cylinder 26 over the length of the needle 14 and preventing removal of the inner cylinder 26 from the outer cylinder 20 during and after needle use. The distal end 30 of inner cylinder 26 has a decreasing diameter portion 44 which allows the aperture 46 of the inner cylinder tip 48 to substantially conform to the diameter of the needle 14. Again, it should be noted that the inner cylinder 26 may be made of a translucent material for clear visibility of the needle 14 during use.

In the preferred embodiment, the inner cylinder tip 48 is beveled or angled to prevent slippage and allow ease of retractability when the needle guard 10 is administered to a body at an angle. Alternatively or additionally, an adhesive or abrasive material 50 may be distributed on the outer surface 38 of the inner cylinder 26 around the decreasing diameter portion 44 to prevent slippage of said inner cylinder tip 48 when initial contact is made with a body. The adhesive material 50 may be any well known adhesive means such as a soft or gummy plastic material such as polypropylene.

Figures 6A, 6B, 6C:
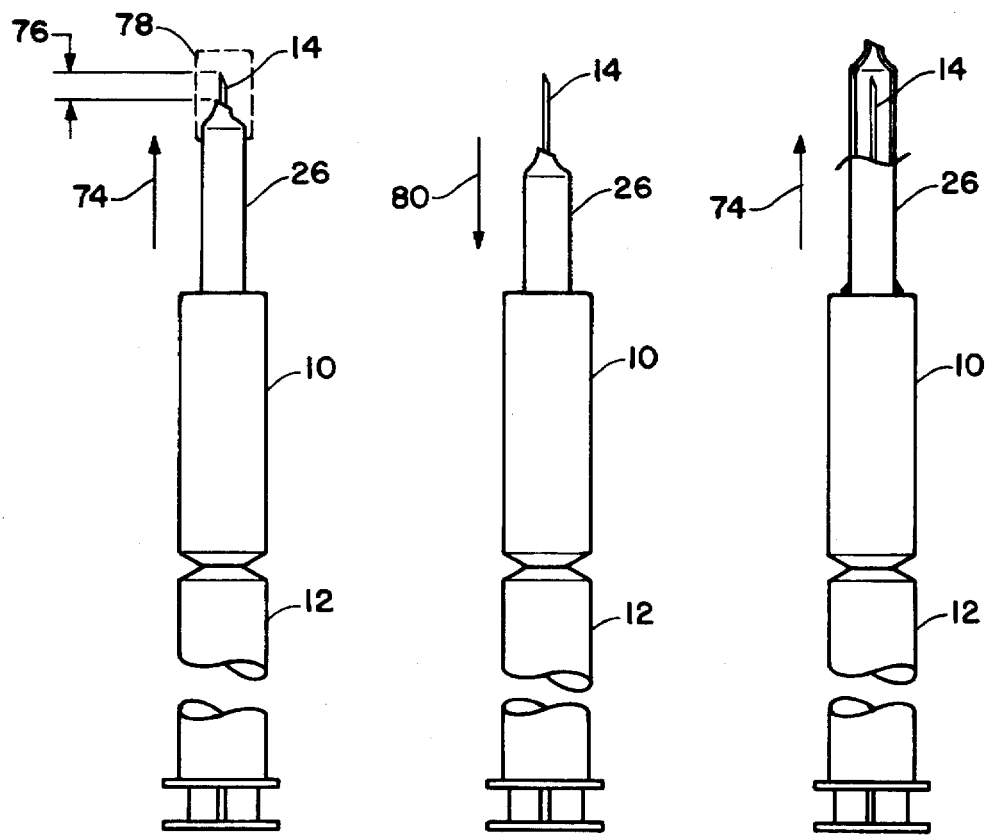
FIG. 6a is a side view of the present invention in an initial usable or retracted position prior to needle administration.
FIG. 6b is a side view of the present invention in an armed or released position during insertion of a needle into a receiving body.
FIG. 6c is a side view of the present invention in an extended irreversible position after the needle is withdrawn from the body.

One or more flexible flaps 52a,b may be carefully positioned on the outer surface 38 of inner cylinder 26 to prevent the inner cylinder 26 from being retracted once the needle guard is in its fully extended position as shown in FIG. 1 and 6c. As shown in FIG. 1, the flaps 52a,b are carefully distanced from the lugs 36a-d to allow just enough room for passage of the flaps 52a,b through the distal end 30 of inner cylinder 26. Although the preferred embodiment teaches the use of flaps 52a,b, other well known means for preventing the retraction of inner cylinder 26 are contemplated by the present invention.

The final major component is a force providing mechanism, such as a spring 54 partially shown in FIG. 2.

Best illustrated in the cross sectional view of FIG. 3, the spring 54 extends from the proximal end 22 of outer cylinder 20 through uniform diameter portion 56 of inner cylinder 26. Alternatively (not shown), the spring 54 may be mounted between the proximal end 22 of the outer cylinder 20 and the proximal end 28 of the inner cylinder 26. The purpose of the spring is to urge the inner cylinder 26 away from the proximal end 22 of outer cylinder 20. The spring 54 may be made of any suitable material, such as metal or plastic, and may be of any suitable, functional shape. It is contemplated that spring 54 may be molded as part of the outer cylinder 20 or inner cylinder 26.

FIG. 3 provides a more detailed illustration of the attachment of the needle guard 10 to the needle retaining device 12. For illustrative purposes only, the needle retaining device 12 includes a Luer tip 58 and a needle hub 60. The flexible rigid tabs 40 of the needle guard 10 are forced over the needle hub 60 for engagement between the Luer tip 58 and the needle hub 60. As has been noted before, although this is one preferred method of attachment, any known method of adapting the needle guard 10 to a needle 14 or needle retaining device 12 is clearly within the contemplation of the present invention.

FIG. 3 also illustrates the lugs 36a–d as positioned in the track 32. However, the track 32 is best illustrated by viewing the exploded view in FIG. 5. The track 32 has three transitional areas which are particularly noteworthy. The first transitional area of the track 32 is a initial usable or retractable portion 62. The second area of the track 32 is an armed or released portion 64. The final area of the track 32 is the extension portion 66. Each of the lugs 36a–d moves in its respective track 32 in a systematic sequential pattern and method as described in more detail below.

The automatic operation of the needle guard 10 is best demonstrated by viewing FIGS. 6a–c in combination with FIG. 5. Prior to administration of the needle into a receiving body, while the needle guard 10 is in its initial usable state as shown in FIG. 6a, the angled lower side 70 of lugs 36a–d are forced up against angled ledge 72 of track 32 by the spring force 74 of spring 54. In this initial position, an exposed needle portion 76 is visible for insertion of the needle into a body. The amount of exposed needle portion 76 may vary depending on the desired use. This exposed needle portion 76 may be protected prior to needle administration by the use of an optional protective cap 78.

Subsequently, when the needle 14 is inserted into the receiving body, an opposing insertion force 80, which is greater then spring force 74, is applied to the distal end 30 of inner cylinder 26 thereby causing the inner cylinder 26 to retract into the outer cylinder 20. The inner cylinder 26 continues retracting until the upper side 82 of lugs 34a–c contact the curvature 84 of track 32. When contact is made between the upper side 82 of lugs 34a–c and the curvature 84 of track 32, the opposing insertion force 80 forces the lugs 34a"d to shift radially causing the lower edge of lugs 34a–d to catch the corner 86 of track 32. This result of this function is shown in second state of FIG. 6b. The distance of the retractable portion 62 and release portion 66 will vary depending on the intended use of the needle retaining device 12.

When the needle is ready for withdraw, the opposing insertion force 80 is removed thereby leaving only the outward spring force 74. The outward spring force 74 forces the lugs 34a–d to slide down slope 73 of track 32 and through the extension portion 66 of track 32. Accordingly, the inner cylinder 26 extends from the outer cylinder 20 until the lugs 34a–d are forced up against the lip 42 of outer cylinder 20. In this third extended safety position, as shown in FIG. 6c, the entire length of the needle 14 is covered and the flaps 52a,b are released thereby providing a locking function to prevent reuse of the needle device.

The present invention also teaches a method for providing an automatic non-reusable needle. The steps of the method include adapting a proximal end of an outer cylinder to a needle retaining device and positioning the inner cylinder in the outer cylinder for movement of the inner cylinder through a distal end of the outer cylinder. The steps further include providing a spring between a proximal end of the inner cylinder and the outer cylinder for urging the inner cylinder away from the proximal end of the outer cylinder. Additional steps include maintaining the inner cylinder in an initial usable position prior to administration of the needle, arming the inner cylinder during insertion of the needle into a body, and finally extending the inner cylinder to an extended irreversible position during withdraw of the needle from the body. The method concludes by automatically locking the inner cylinder in the extended irreversible position after the needle is fully withdrawn.

Having described the preferred embodiment of the invention, it will be apparent to one of skill in the art that other embodiments incorporating their concepts may be used. Accordingly, the invention should be limited only by the spirit and scope of the appended claims.

I claim:

1. An automatic non-reusable needle guard comprising:
    a first cylinder adaptable to a needle retaining device, said needle retaining device having a needle extending therefrom for inserting into a receiving body;
    a second cylinder operable with said first cylinder for movement of said second cylinder from a first resting position wherein said needle has an exposed needle portion to a second position wherein said second cylinder is retracted from said first position to further increase said exposed needle portion and further to a third position wherein said second cylinder is extended to fully cover said exposed needle portion; and
    a mechanism for retracting said second cylinder from said first resting position and automatically releasing said second cylinder from said second position during insertion of said needle into said receiving body for movement of said second cylinder to said third position as said needle is withdrawn from said body.

2. An automatic non-reusable needle guard as recited in claim 1, wherein said first cylinder is an outer cylinder and said second cylinder is an inner cylinder.

3. An automatic non-reusable needle guard as recited in claim 2, wherein said outer cylinder is integrally formed in said needle retaining device.

4. An automatic non-reusable needle guard as recited in claim 2, wherein said outer cylinder is attached to said needle retaining device.

5. An automatic non-reusable needle guard as recited in claim 2, wherein said mechanism comprises:
    a track formed in said outer cylinder;
    at least one lug located on said inner cylinder, said lug positioned in said track for guiding said inner cylinder from said first resting position to said second position and further to said third position; and
    a spring coupled to said inner cylinder for urging said inner cylinder from said outer cylinder thereby moving said inner cylinder from said second position to said third position.

6. An automatic non-reusable needle guard as recited in claim 1, wherein said needle retaining device is a syringe.

7. A protective needle guard for use before, during and after needle administration, comprising:

an outer cylinder coupled to a needle;

an inner cylinder adaptable to said outer cylinder for automatic sequential movement of said inner cylinder from a resting retractable position wherein said needle has an exposed needle portion to a released position wherein said inner cylinder is retracted and further to an extended locked position wherein said inner cylinder covers said exposed needle portion; and a mechanism for maintaining said inner cylinder in said resting retractable position prior to needle administration, movement of said inner cylinder to said released position during insertion of said needle into a body, and extending said inner cylinder to said extended locked position during withdraw of said needle from said body.

8. A non-reusable needle safety guard comprising:

an inner cylinder having an aperture extending longitudinally from a proximal end to a distal end for passage of a needle therethrough, said inner cylinder having an outer surface wherein at least one protruding member is formed on said outer surface of said inner cylinder;

an outer cylinder for containing said inner cylinder, said outer cylinder having an inner surface wherein a track is formed thereon for engagement with said at least one protruding member, said outer cylinder having a proximal end and a distal end, wherein said proximal end is coupled to said needle and said distal end has an aperture for movement of said inner cylinder from a retractable position wherein said needle has an exposed needle portion to released position wherein said inner cylinder is retracted to increase said exposed needle portion and further to an extended locked position wherein said inner cylinder covers said exposed needle portion; and a spring disposed within said inner cylinder and coupled to said proximal end of said outer cylinder for maintaining said inner cylinder in said retractable position prior to needle administration, and urging said inner cylinder from said released position to said extended locked position during withdraw of said needle from said body.

9. A non-reusable needle safety guard as recited in claim 8, wherein said at least one protruding member is a lug.

10. A non-reusable needle safety guard as recited in claim 8, wherein said at least one protruding member is positioned proximate to said proximal end of said inner cylinder.

11. A non-reusable needle safety guard as recited in claim 8, wherein said at least one protruding member is positioned proximate said distal end of said inner cylinder.

12. A non-reusable needle safety guard as recited in claim 8, wherein said at least one protruding member is a plurality of protruding members.

13. A non-reusable needle safety guard as recited in claim 8, wherein said distal end of said outer cylinder has a lip portion for preventing removal of said inner cylinder from said outer cylinder.

14. A non-reusable needle safety guard as recited in claim 8, further comprising a locking mechanism for preventing retraction of said inner cylinder after said inner cylinder is extended in said extended locked position.

15. A non-reusable needle safety guard as recited in claim 8, wherein said locking mechanism is a flexible flap positioned on said outer surface of said inner cylinder.

16. A non-reusable needle safety guard as recited in claim 8, wherein a portion of said inner cylinder proximate to said distal end decreases in diameter to substantially conform to a diameter of said needle.

17. A non-reusable needle safety guard as recited in claim 8, wherein said distal end of said inner cylinder has a angled tip.

18. A non-reusable needle safety guard as recited in claim 8, wherein said distal end of said inner cylinder has an adhesive material applied thereon.

19. A non-reusable needle safety guard as recited in claim 8, further comprising a locking mechanism for providing irreversibility of said inner cylinder after said inner cylinder has been fully extended.

20. A method for providing an automatic non-reusable needle guard, comprising the steps of:

adapting a proximal end of an outer cylinder to a needle retaining device;

positioning an inner cylinder in said outer cylinder for movement of said inner cylinder through a distal end of said outer cylinder;

maintaining said inner cylinder in an initial usable position wherein said needle is partially exposed prior to needle administration;

moving said inner cylinder from said initial usable position to a retracted position wherein said needle is fully exposed during insertion of a needle into a body;

automatically releasing said inner cylinder from said retracted position; and extending said inner cylinder to an extended irreversible position during withdraw of said needle from said body.

21. A method as recited in claim 20, further comprising the step of automatically locking said inner cylinder in said extended irreversible position after withdraw of said needle.

* * * * *

UNITED STATES PATENT AND TRADEMARK OFFICE
CERTIFICATE OF CORRECTION

PATENT NO. : 5,688,241
DATED : November 18, 1997
INVENTOR(S) : Asbaghi

It is certified that error appears in the above-identified patent and that said Letters Patent is hereby corrected as shown below:

On the title page, item [76] Inventor: insert the following
-- Alidad Far Tash, 830 Childs Way, #700 Los Angeles, CA 90089 --

Signed and Sealed this

Seventeenth Day of March, 1998

Attest:

BRUCE LEHMAN

Attesting Officer

Commissioner of Patents and Trademarks